(12) United States Patent
Chae

(10) Patent No.: US 7,101,700 B2
(45) Date of Patent: Sep. 5, 2006

(54) PEPTIDE VECTOR

(76) Inventor: Young-Jin Chae, 1202 Union Center 837-11 Yeoksam-dong, Kangham-ku, Seoul (KR) 135-754

( * ) Notice: Subject to any disclaimer, the term of this patent is extended or adjusted under 35 U.S.C. 154(b) by 270 days.

(21) Appl. No.: 10/071,476

(22) Filed: Feb. 8, 2002

(65) Prior Publication Data

US 2003/0096738 A1    May 22, 2003

(30) Foreign Application Priority Data

Feb. 10, 2001   (KR) ................................ 2001-6587

(51) Int. Cl.
 *C12N 7/01*    (2006.01)
(52) U.S. Cl. ................ 435/235.1; 435/320.1; 435/456
(58) Field of Classification Search ............ 435/320.1, 435/69.1; 514/44
See application file for complete search history.

(56) References Cited

U.S. PATENT DOCUMENTS 5,736,392 A * 4/1998 Hawley-Nelson et al. ........... 435/320.1

OTHER PUBLICATIONS

Anderson Human Gene Therapy Nature vol. 392, supp 1998 pp. 25-30.*
Palu et al. In Pursuit of New Developments for Gene Therapy of Human Disease J. of Biotech. vol. 68 1999 pp. 1-13.*
Verma et al. Gene Therapy—promises, problems and prospects Nature vol. 389 1997 p. 239-242.*

* cited by examiner

Primary Examiner—James Ketter
(74) Attorney, Agent, or Firm—Jones Day

(57) ABSTRACT

The present invention relates to a peptide vector comprising a leader peptide, a linker DNA, and a desired gene. This peptide vector can achieve gene transfer without cell specificity and does not induce host immune responses.

6 Claims, 1 Drawing Sheet

[FIG. 1]
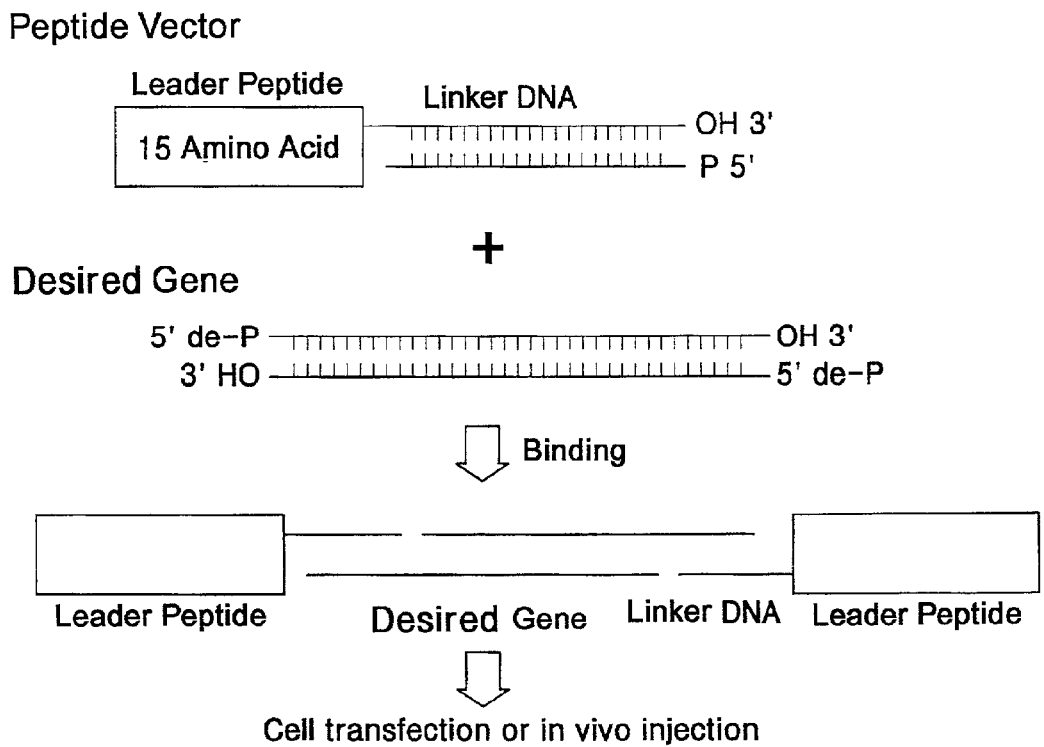
[FIG. 2]
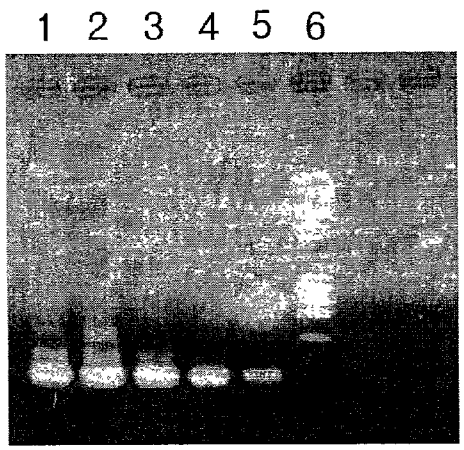

PEPTIDE VECTOR

BACKGROUND OF THE INVENTION

The invention relates to a peptide vector which can achieve gene transfer without cell specificity and does not induce host immune responses.

It is known that viral vectors have been mainly used for introducing genes into a living body, by using their cell endosmosis ability. These viral vectors include, for example, adenovirus, herpes virus, retrovirus, and the like.

Adenovirus is a non-enveloped double-stranded DNA virus, and causes insignificant upper respiratory tract infections, keratoconjunctivitis, enterogastritis, and the like in human. The adenovirus genomes are approximately 36 kb, and easy to handle by using conventional recombinant DNA technology. Cell endosmosis of virus is initialized by binding of a fiber knob protein of adenovirus to Coxsackie & Adenovirus receptor (CAR) on the cell surface. Subsequently, via the interactions between integrins ($\alpha$ v$\beta$ 3, $\alpha$ v$\beta$ 5) on the cell surface and the capsid penton base, the virion is introduced into the cell by the clathrin coated endocytosis. Then, the conforrnational changes of virion capsid proteins are derived, as the low pH condition of the endosome, allowing the release of the virion capsid proteins to the cytoplasm. Following the protein release, the capsid proteins translocate to the nucleus, where its replication and transcription are carried out. Transcription of genes can be divided into two different types, for early genes (E) which are expressed before the replication, and late genes (L) which are expressed after the replication. Adenovirus used for gene therapy lacks the E1 gene area, resulting incomplete replication, thereby being used in a form containing other DNAs inserted thereto. Therefore, the recombinant adenovirus vectors can be cultured to increase, in cell lines such as HEK293 which can express E1 genes continuously.

Retrovirus with envelope is a single stranded RNA virus having a diploid genome of about 7~10 kb, and comprises the four gene groups called gag, pro, pol, and env, respectively. Each of the gene group encodes the structural capsid protein, viral protease, integrase, reverse transcriptase, envelope and glycoprotein, etc. The retrovirus has a packing signal ($\psi$) referred as long-terminal repeat (LTR), and a cis-acting sequence. Retrovirus infection of a cell can be achieved by primarily, binding of the envelope glycoprotein to its cell surface receptor, and subsequent fusing of the virus envelope with the cell membrane, thereby internalizing the capsid nucleus into the cell. Once the capsid has entered into the cytoplasm, the reverse transcriptase inside the capsid produces double stranded proviral genome, which forms a complex with an integrase and moves to the nuclear membrane. When the nuclear membrane disappears during mitosis, the complex enters into the nucleus. The proviral genome introduced into the nucleus inserts into chromosome of the host by means of an integrase, to express the viral genome by using the transcription apparatus of the host. The recombinant retrovirus vector does not express any viral gene, that makes this distinguished from the above-mentioned adenovirus vectors, as all of its genes are replaced to marker or therapeutic genes except LTRs and $\psi$ sequence. To cultivate such recombinant retrovirus, the viral genes of gag, pol, and env should be expressed in a trans form, which can be achieved by using cell lines that express these genes in stable manner.

Adeno-binding virus belongs to a parvoviridae family, and is a simple virus having short single stranded DNA genome. The adeno-binding virus is comprised of two open reading frames (ORF) which are rep (control) and cap (structure), and two inverted terminal repeats (ITRs). The inverted terminal repeats are the only part needed for encapsidation and integration into the host genome, being stably integrated into the 19th human chromosome. However, the virus does not have self-growth ability, so it can be only grown under the presence of helper virus such as adenovirus or herpesvirus, etc. The recombinant adeno-binding virus is formed by the co-transfection with a plasmid having a transcription unit inserted between the inverted terminal repeats, and a plasmid containing a rep and cap open reading frames, and in this time, a sub-infection with a helper virus such as adenovirus is needed. After purifying process of recombinant adeno-binding virus, it can be used for gene therapy applications.

Herpes simplex virus-1 is a double stranded DNA virus having envelope. It encodes 80 or more genes from its 152 kb genomes, and has a significantly wide range of hosts as its envelope glycoproteins (gB, gC) bind to the extracellular heparan sulphate, that is discovered from the all kinds of cell membrane. When the virus is being entered into the host cell, the virus envelope glycoprotein gD and the fibroblast growth factor (FGF) receptor of the host are necessary. Herpes simplex virus vector can be divided into two types, a recombinant herpes simplex virus vector and an amplicon vector, wherein the recombinant herpes simplex virus vector has a transcription unit directly inserted in its genome, and the amplicon vector is a plasmid infected with a helper virus, wherein the said plasmid contains the transcription unit, replication origin, and packing signal. The amplicon vector is subjected to the rolling circle replication, producing a herpes simplex virus having an insertion of multiple copy genes during packing procedure.

Those above-mentioned virus vectors have their own advantages and disadvantages. Common problems to these above virus vectors include the limitation of the cell ranges, which could be infected by them, i.e. the limitation in cells which could receive them, and the inactivation by immune responses of host. As these types of vectors have such limitations, they are not applicable to all kinds of cells.

Therefore, there have been many efforts to overcome these problems, and most of them are directed to modify the native tropism of a virus to infect a specific cell or to express transgenes in only specific cell, using a cell type specific promoter. However, there have been no satisfying results in any of those efforts.

SUMMARY OF THE INVENTION

An object of the present invention is to provide a peptide vector without cell specificity.

Additional object of the present invention is to provide a peptide vector that does not induce host cellular immune responses.

Still another object of the present invention is to provide a method of producing a peptide-DNA complex comprising covalently linking the peptide of SEQ ID NO:1 and the DNA of SEQ ID NO:2, and hybridizing the DNA of SEQ ID NO:3 to the DNA of SEQ ID NO:2.

Further object of the present invention is to provide a method of introducing and expressing a desired gene comprising infecting target cells with a peptide vector which comprises a leader peptide, a linker DNA, and a desired gene.

In order to achieve these and other objects, the present invention provides a peptide vector which comprising a leader peptide, a linker DNA, and a desired gene.

DETAILED DESCRIPTION OF THE INVENTION

The present invention is related to a peptide vector which can achieve gene transfer without cell specificity, and does not induce host immune responses.

The peptide vector according to the present invention is composed of a leader peptide, a linker DNA, and a desired gene. The leader peptide (SEQ ID NO:1) has a structure shown below, the amino acid sequence was deduced by analyzing proteins which are expected to have a fusion ability of cell membrane in various viruses having envelope, for example, retrovirus, paramixovirus and the like. This sequence is introduced into a cell directly through the cell membrane.

<Leader Peptide: SEQ ID NO:1>

| | | | | | | | | | | | | | | | | |
|---|---|---|---|---|---|---|---|---|---|---|---|---|---|---|---|---|
| | Ac-Gly-Leu-Gly-Ile-Ser-Tyr-Gly-Arg-Lys-Lys-Arg-Arg-Gly-Arg-Arg-Cys | | | | | | | | | | | | | | | |
| | 1 | 2 | 3 | 4 | 5 | 6 | 7 | 8 | 9 | 10 | 11 | 12 | 13 | 14 | 15 | 16 |
| (mutant) | | Ile | | Leu | | | | | | Arg | Lys | | Leu | | | |
| | | | | | | | | | | | | | Ile | | | |
| | | | | | | | | | | | | | Arg | | | |
| | | | | | | | | | | | | | Gla | | | |
| | | | | | | | | | | | | | Asn | | | |
| | | | | | | | | | | | | | Ser | | | |

* N-terminal acetylation (Ac): attaching an acetyl group to N-terminal amine group in order to eliminate the reaction with other molecules.
* C-terminal Cys: attaching a cystein (Cys) to C-terminal in order to bind the linker DNA with S-S bond.

The four amino acids of N-terminal are non-polar and have aliphatic side chains, so that it can make its easy entry to the cell membrane, and next two (5th, and 6th) amino acids are polar and they no electric charges so that they can maintain their stability, when those 1st to 4th amino acids are inserted. 7th to 15th amino acids are selected from mainly basic amino acids having pKa value of 10 or more, so that they can be driven into the cell through the negative charges inside the cell. 13th amino acid can be an amino acid which has a side chain being polar without charge (Asn, Gln, and Ser, etc.), or has an aliphatic side chain with non-polarity (Ala, Leu, and Ile, etc.), or has a basic side chain (Arg, etc.), any one of those amino acids does not affect its overall function. A peptide having such structure ultimately can be applied to all kinds of cells having membrane structure, as it is introduced into a cell not by binding with the membrane receptor, but by penetrating directly into the cell membrane.

The linker DNA, composed of 15 to 18 bases, connects a leader peptide and a desired gene, and has a structure as below.

linker-1 (SEQ ID NO:2): 5'-Cys-CTA-ATA-CGA-CTC-ACT-AT-3' linker-2 (SEQ ID NO:3): 3'-GA—TAT—GCT—GAG—TGA—T-5'

For linker-1, cystein is conjugated to 5' end for binding with the leader peptide, and for linker-2, phosphate group is attached to 5' end by using T4 polykinase for binding with the desired gene.

Only one strand (linker-1, SEQ ID NO:2) of complementary double strand of the linker DNA is covalently bonded with a leader peptide, thus when the linker is binding with the desired gene, only the other strand (linker-2, SEQ ID NO:3) which is not covalently bonded with the leader peptide, can be covalently bonded with the desired gene, so it can be easily separated from the leader peptide under the inner environment of the nucleus. Thus, both ends of separated genes are single-stranded, it is possible to be readily integrated into the inner part of the host chromosome later.

Preventing the desired gene from binding with the linker-1DNA during its binding process with the vector can be achieved by removing the phosphate group at 5' end using alkaline phosphatase.

Carrying out filling and terminal adenylation by using a Taq polymerase, in order to fill the overhangs formed in the course of digestion by restriction enzyme, makes the binding convenient, as the terminal adenylation is complementary to T overhang of the linker DNA during its binding with a vector.

Genes with various purposes such as for therapy, and for specific character expression etc, can be used as a desired gene. Promoter and enhancer can be suitably chosen for the selected genes corresponding to the each purpose.

The appropriate injection level of the complex comprised of a vector and trans genes is determined according to the degree of acute toxicity derived from the complex. Whether transgenes are transmitted and expressed is observed by sampling DNA and mRNA from cerebrum, cerebellum, liver, kidney, heart, lung, muscle, and spermary, etc, and carrying out PCR and RT-PCR technology.

FIG. 1 illustrates the binding mechanism between the peptide vector and a desired gene according to the present invention.

The present invention is described with more detail in reference to the following examples, but they are not intended to limit the scope of present invention.

BRIEF DESCRIPTION OF THE DRAWINGS

FIG. 1 shows the binding mechanism between peptide vector and a desired gene according to the present invention.

FIG. 2 shows the expression level of mRNA of transferred marker gene by peptide vector in brain and muscle tissues, detected by PCR.

DETAILED DESCRIPTION OF THE PREFERRED EMBODIMENT

EXAMPLE 1

Synthesis of Peptide Vector

Leader peptide (SEQ ID NO:1) was synthesized by Fmoc-solid phase method.

To linker-1 DNA (SEQ ID NO:2), cystein was attached in order for binding with the leader peptide, and to the 5' end of linker-2 DNA (SEQ ID NO:3), phosphate group was attached by T4 polykinase in order for binding with the marker gene.

Leader peptide and linker-1 DNA of 2 nmols respectively, were reacted in buffer solution(50 mM Tris, 0.1 mM EDTA, 10 mM DTT, pH 10.5), at 37° C. for 1 hour to bind via S-S bond. After adding 2 nmols of linker-2 DNA to the above solution, it was further reacted at 60° C. for 30 minutes to carry out hybridization of linker-1 DNA and linker-2 DNA, which was kinated at 5' end. Then, the resulted solution was aliquoted to 100 pmols (20 pmols/ul), and maintained below −20° C.

EXAMPLE 2

Preparation of Marker Gene

Plasmid was extracted from cultured *E. coli* transformed with pCX-GFP, using the Quagen kit. The extracted plasmid was treated with Bam H1 and Sal I to remove the GFP containing part, then subjected to electrophoresis using 0.8% agarose gel. A band of marker part was cut and purified with silica.

5 µg of purified GFP genes were treated with alkaline phosphatase to remove 5' phosphate group. After completing the alkaline phosphatase reaction, it was further purified by using phenol/chloroform/isoamylalcohol solution, then precipitated and purified with isopropanol and ethanol. In order to fill overhangs formed in the course of digestion by restriction enzyme, filling and terminal adenylation were carried out by using Taq polymerase. Then, it is again, purified with phenol/chloroform/isoamyl alcohol solution, and isopropanol and ethanol.

EXAMPLE 3

Binding of vector and marker gene 100 pmols of vector obtained from the example 1 and 2 µg of marker gene obtained from the example 2 were reacted for binding, in binding buffer solution(50 mM Tris-HCl, 10 mM $MgCl_2$, 10 mM DTT, 1 mM ATP, pH 7.5) at 16° C. for 4 hours by using T4 ligase.

EXAMPLE 4

Extraction of mRNA and Determination with RT-PCR

The expression of transgenes injected into each tissue was investigated by PCR after extracting mRNA from brain and muscle tissue, and synthesizing cDNA.

The transgenes obtained from the example 3 were intravenously injected to a male mouse (200 g weight) with a dose of 500 ng/day, at day 1, 3, and 5, then the mouse was euthanized at day 6. mRNA was extracted from brain, and muscle tissue samples of the mouse, by using mRNA purification kit (Ambion™,Inc. (Austin, Tex.), Cat No. 1918).

1 µg of the extracted mRNA, 50 pmols of oligo-dt or random primer and RNase inhibitor (40 units) were added thereto, and the total volume was adjusted to 50 µl by adding distilled water, denatured at 96° C. for 10 minutes, and annealed at 60° C. for 30 minutes. Reaction buffer, 1.25 mM of dNTP, 2 mMs DTT, RNase inhibitor (40 units), and MMLV reverse transcriptase (Ambion™, Inc. (Austin, Tex.)) were added thereto, and reacted at 42° C. for 1 hour. After completing the reaction, it was precipitated and purified by isopropanol and ethanol, and resuspended into distilled water.

After synthesizing cDNA, PCR was performed using GFP specific primer [GFP-f(SEQ ID NO:4), GFP-r(SEQ ID NO:5)] was performed by Taq polymerase(TaKaRa™ Bio. Inc. (Japan)). After completing the PCR, electrophoresis was carried out on the 2% agarose gel to find a band.

<GFP specific primer>

GFP-f: 5'-TGAAGGTGATGCAACATACGG-3'(SEQ ID NO:4)

GFP-r: 5'-GTCTTGTAGTTCCCGTCATC-3'(SEQ ID NO:5)

The result of PCR was shown in FIG. 2: lane 1 for brain, lane 2 for muscle, lane 3 and 4 for negative controls, lane 5 for positive control, and lane 6 for size markers. The size markers shown are 1353, 1078, 872, 603, 310, 281, 271, 234, 194, 118, and 72 bp from top to bottom.

As it can be seen from FIG. 2, strong band of GFP cDNA was observed at 234 bp position of lane 1(brain), and lane 2(muscle). Therefore, it can be seen that it is effectively expressed at brain and muscle tissue.

The peptide vector according to the present invention can transmit genes to all kinds of cells without tissue specific tropism, unlike conventional virus vectors and does not induce host immune responses, due to its small size corresponding to the level of a hapten.

The peptide vector according to the present invention can be extensively applied to various fields, for example, applications to gene therapy, gene transfection during general cell culture, and production of transduced animal or plant, accelerating the study related to gene functions, which is being conducted after the completion of the human genome project.

What is claimed is:

1. A peptide vector comprising a leader peptide, a linker DNA, and a desired nucleic acid sequence, wherein said linker DNA is double-stranded, and wherein only one strand of said linker DNA is covalently bound to said leader peptide, and wherein the leader peptide comprises SEQ ID NO:1 or a variant of SEQ ID NO:1 in which the amino acid residue at position 2 is isoleucine; position 4 is leucine; position 10 is arginine; position 11 is lysine; or position 13 is leucine, isoleucine, arginine, glutamine, asparagine or serine; or a combination of any of the foregoing.

2. The peptide vector according to claim 1, wherein the linker DNA comprises SEQ ID NO:2 and SEQ ID NO:3.

3. A peptide vector comprising a peptide having the sequence shown in SEQ ID NO:1, or a variant of SEQ ID NO:1 in which the amino acid residue at position 2 is isoleucine; position 4 is leucine; position 10 is arginine; position 11 is lysine; or position 13 is leucine, isoleucine, arginine, glutamine, asparagine or serine; or a combination of any of the foregoing, a DNA having the sequence shown in SEQ ID NO:2, and a DNA having the sequence shown in SEQ ID NO:3.

4. A method of producing a peptide vector comprising: covalently linking a peptide having the sequence shown in SEQ ID NO:1 or a variant of SEQ ID NO:1 in which the amino acid residue at position 2 is isoleucine; position 4 is leucine; position 10 is arginine; position 11 is lysine; or position 13 is leucine, isoleucine, arginine, glutamine, asparagine or serine; or a combination of any of the foregoing; and a DNA having the sequence shown in SEQ ID NO:2; and hybridizing a nucleic acid having the DNA sequence shown in SEQ ID NO:3 to a nucleic acid having the DNA sequence shown in SEQ ID NO:2.

5. A method of introducing and expressing in a target cell in vitro a desired nucleic acid sequence comprising infecting said target cell with a peptide vector which comprises a leader peptide, a linker DNA, and a desired nucleic acid sequence, wherein said linker DNA is double-stranded, and wherein only one strand of said linker DNA is covalently bound to said leader peptide, and wherein the leader peptide comprises SEQ ID NO:1 or a variant of SEQ ID NO:1 in which the amino acid residue at position 2 is isoleucine; position 4 is leucine; position 10 is arginine; position 11 is lysine; or position 13 is leucine, isoleucine, arginine, glutamine, asparagine or serine; or a combination of any of the foregoing.

6. The method according to claim 5, wherein the linker DNA comprises a DNA having the sequence shown in SEQ ID NO:2, and a DNA having the sequence shown in SEQ ID NO:3.

* * * * *

SEQUENCE LISTING

<160> NUMBER OF SEQ ID NOS: 5

<210> SEQ ID NO 1
<211> LENGTH: 16
<212> TYPE: PRT
<213> ORGANISM: Artificial
<220> FEATURE:
<223> OTHER INFORMATION: Description of Artificial Sequence: Leader
      peptide deduced from peptides with fusion ability
<220> FEATURE:
<223> OTHER INFORMATION: N-terminal Gly is acetylated
<220> FEATURE:
<221> NAME/KEY: SITE
<222> LOCATION: 2, 4
<223> OTHER INFORMATION: Xaa = Leu or Ile
<220> FEATURE:
<221> NAME/KEY: SITE
<222> LOCATION: 10, 11
<223> OTHER INFORMATION: Xaa = Arg or Lys
<220> FEATURE:
<221> NAME/KEY: SITE
<222> LOCATION: 13
<223> OTHER INFORMATION: Xaa = Gly, Leu, Ile, Arg, Gln, Asn, Ser

<400> SEQUENCE: 1

Gly Xaa Gly Xaa Ser Tyr Gly Arg Lys Xaa Xaa Arg Xaa Arg Arg Cys
1               5                   10                  15

<210> SEQ ID NO 2
<211> LENGTH: 17
<212> TYPE: DNA
<213> ORGANISM: Artificial
<220> FEATURE:
<223> OTHER INFORMATION: Description of Artificial Sequence: Linker
<220> FEATURE:
<223> OTHER INFORMATION: Linker DNA: 5' end of C forms ester bond with
      Cys

<400> SEQUENCE: 2
ctaatacgac tcactat                                                 17

<210> SEQ ID NO 3
<211> LENGTH: 16
<212> TYPE: DNA
<213> ORGANISM: Artificial
<220> FEATURE:
<223> OTHER INFORMATION: Description of Artificial Sequence: Linker

<400> SEQUENCE: 3
tagtgagtcg tattag                                                  16

<210> SEQ ID NO 4
<211> LENGTH: 20
<212> TYPE: DNA
<213> ORGANISM: Artificial
<220> FEATURE:
<223> OTHER INFORMATION: Description of Artificial Sequence: Primer

<400> SEQUENCE: 4
tgaaggtgat gcaacatacg                                              20

<210> SEQ ID NO 5
<211> LENGTH: 20
<212> TYPE: DNA
<213> ORGANISM: Artificial
<220> FEATURE:
<223> OTHER INFORMATION: Description of Artificial Sequence: Primer -continued

```
<400> SEQUENCE: 5
gtcttgtagt tcccgtcatc                                              20
```